United States Patent [19]

Lutz et al.

[11] 4,037,107
[45] July 19, 1977

[54] X-RAY DIAGNOSING APPARATUS WITH SEVERAL PHOTOGRAPHING SYSTEMS SELECTIVELY CONNECTABLE TO A COMMON GENERATOR

[75] Inventors: Herbert Lutz, Seukendorf; Manfred Pfeiler, Erlangen, both of Germany

[73] Assignee: Siemens Aktiengesellschaft, Berlin & Munich, Germany

[21] Appl. No.: 630,787

[22] Filed: Nov. 11, 1975

Related U.S. Application Data

[63] Continuation-in-part of Ser. No. 446,689, Feb. 28, 1974, abandoned.

[51] Int. Cl.² .............................................. H05G 1/00
[52] U.S. Cl. ................................. 250/402; 250/416 R
[58] Field of Search .............. 250/401, 402, 407, 408, 250/409, 413, 414, 416

[56] References Cited

U.S. PATENT DOCUMENTS

| | | | |
|---|---|---|---|
| 2,171,134 | 8/1939 | Timmons | 250/407 |
| 3,770,963 | 11/1973 | Vandervelden | 250/409 |

Primary Examiner—Craig E. Church
Attorney, Agent, or Firm—Hill, Gross, Simpson, Van Santen, Steadman, Chiara & Simpson

[57] ABSTRACT

An X-ray diagnosing apparatus has several photographing systems which can be selectively connected to a common generator. Each system is provided with an operating desk for setting the photographing data and means for connecting the corresponding X-ray tube to the generator and for operating further auxiliary devices. The invention is particularly characterized in that each operating desk has an indicating area with at least one signaling lamp for the correlated X-ray tube and the correlated auxiliary devices. Furthermore, means are provided for operating the signaling lamps to indicate operational readiness and a proper operation of the X-ray tube and auxiliary devices.

3 Claims, 6 Drawing Figures

X-RAY DIAGNOSING APPARATUS WITH SEVERAL PHOTOGRAPHING SYSTEMS SELECTIVELY CONNECTABLE TO A COMMON GENERATOR

This application is a continuation-in-part of a copending patent application Ser. No. 446,689, filed Feb. 28, 1974, now abandoned.

This invention relates to an X-ray diagnosing apparatus with several photographing systems which can be selectively connected to a common generator, each system having an operating desk for setting the photographing data and means for connecting the corresponding X-ray tube to the generator and for operating further auxiliary devices.

An X-ray diagnosing apparatus of this type is described in the magazine "Electromedica" 3, 1971, pages 83–85. This known X-ray diagnosing apparatus has functional keys located at the operating desks for setting the photographing data according to organic program. Furthermore, each operating desk has a key for selecting a central desk. All photographing data are freely selectable in the central desk.

A drawback of this known X-ray diagnosing apparatus is that there is no control from an operating desk as to whether the preselected devices connected with the high-voltage generator operate properly. Furthermore, in known X-ray diagnosing devices, the screen of the X-ray tube and the functional readiness of the photographing camera can be controlled only with difficulties. For that purpose, the preselected photographing device must be directly supervised.

An object of the present invention is the provision of an X-ray diagnosing device of that described type which makes it possible, by the use of individual operating desks, to provide a simple supervision of the corresponding photographing devices concerning the operational readiness and a proper operation.

Other objects will become apparent in the course of the following specification.

In the accomplishment of the objectives of the present invention, it was found advisable to provide each servicing desk with an indicating area having at least one signaling lamp for the corelating X-ray tube and the corelated auxiliary devices, means being provided for operating the signaling lamps to indicate operational readiness and a proper operation of the X-ray tube and the auxiliary devices.

Thus, according to the X-ray diagnosing apparatus of the present invention, it is possible to control at the operating desk the corresponding X-ray tube and the corresponding auxiliary devices by a single look. Thus, the operator does not have to leave the operating desk for this control.

The invention will appear more clearly from the following detailed description when taken in connection with the accompanying drawings, showing by way of example only, a preferred embodiment of the inventive idea.

Figure 1:
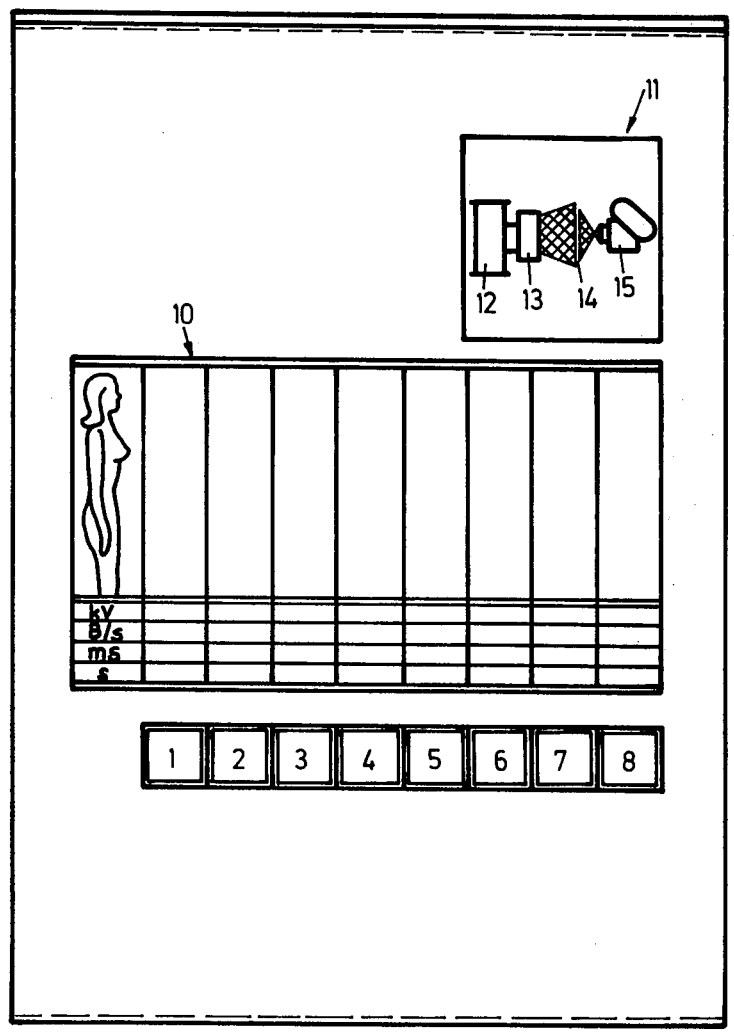
FIG. 1 is a top view of an operating desk of an X-ray diagnosing apparatus of the present invention.

The operating desk of FIG. 1 is combined with an X-ray examining device consisting of an X-ray tube, an X-ray image intensifier and a film photographing camera. The X-ray tube of this X-ray examining device can be switched to a central high-voltage generator which can be used to feed selectively a plurality of X-ray tubes. The operation of the central high-voltage generator takes place in a known manner by a switch on the servicing desk, which is not shown in FIG. 1. The operating desk has operational keys 1 to 8, which make possible an organic programmed selection of photographing data. The keys are operated in the manner described in the above-mentioned "Electromedica" article. The body parts and organs related to the operational keys 1 to 8 are indicated upon a chart 10, at the edge of which a human body is drawn. This illustration of a human body makes easier the location of body parts and organs pertaining to the operational keys 1 to 8.

The operating desk has an indicating area 11, upon which are illuminated a picture of the X-ray tube 12, of the diaphragm 13, of the ray passage 14 and of the film camera 15.

Figure 2:
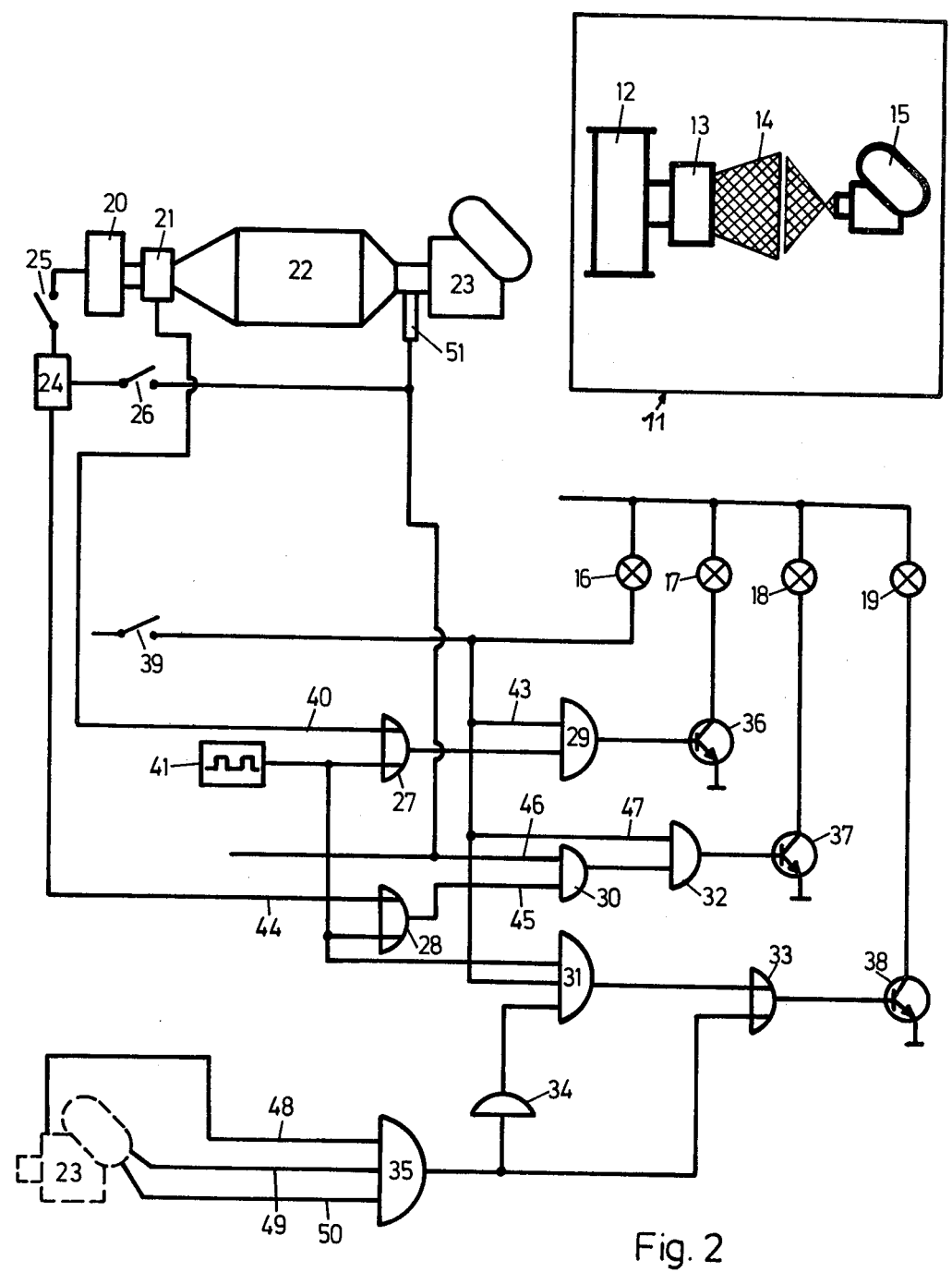
FIG. 2 is a switch circuit showing the supervising members of the servicing desk of FIG. 1.

For illumination purposes serve four lamps 16 to 19, which are combined with these pictures in the manner shown in FIG. 2. Thus, the lamp 16 illuminates the picture of the X-ray tube 12, the lamp 17 illuminates the picture of the diaphragm 13, and so on.

FIG. 2 shows diagrammatically the photographing device combined with the operating desk of FIG. 1, and having the X-ray tube 20, the diaphragm 21, the X-ray image intensifier 22, and the film camera 23. The central high-voltage generator indicated as 24 can be switched to the illustrated photographing system by switches 25 and 26.

A system of gates 27 to 35 is used for operating the lamps 16 to 19 in connection with switch transistors 36 to 38.

The operation of the diaphragms is well known and is described for instance in the German specification No. 2,124,035.

The lamp 16 is lit continuously when the switch 39 is closed, namely when the photographing system has been selected, and thus, the switches 25 and 26 are also closed. Thus, permanent light behind the picture 12 of the X-ray tube means that the photographing system of FIG. 2 has been properly connected to the central high-voltage generator 24.

When the diaphragm 21 is up, a signal is transmitted through the line 40, the OR gate 27, the AND gate 29 and the switch transistor 36, which provides continuous switching on of the lamp 17 and thus continuous light behind the picture 13 of the diaphragm 21. A pulse generator 41 is then inoperative, since the incoming signal lies at the output of the OR gate 27 upon the line 40. The AND gate 29 transmits this signal since its second input receives through the line 43 a signal indicating the readiness of the photographing system.

The OR gate 28 receives at its input 44 a continuous signal which indicates that a balance has been reached by the dose control device during the making of cinema photographs. The signal disappears at the inlet 44 of FIG. 2 when regulating limits have been reached within a regulation of dose output is possible. This continuous signal is switched upon the input 45 of the AND gate 30. At the input 46 of the AND gate 30, there is a signal which indicates the appearance of rays. Thus, when during the preparation of a cinema photographic sequence, a balance has been reached by the dose control device and fluoroscopy takes place, the AND gate 30 supplies a corresponding signal to the AND gate 32. The AND gate 32 opens the switch transistor 37 when the photographing system has been properly selected, since there is a corresponding signal at its input 47. Thus, the lamp 18 lights up quietly and illuminates the picture 14 of the rays when the photographing system has been properly selected, when X-rays appear during the making of a series of pictures, and when a balance has been reached by the dose control device.

If, during the preparation for a cinema-photographing sequence, no balance has been reached by the dose control device, then, there is no signal at the input 44, so that the pulse generator 41 is connected by the OR gate 48, the AND gate 30 and the AND gate 32 to the switch transistor 37. Thus, when there is no balance, the lamp 18 blinks, as well as the picture 14 of the rays.

The AND gate 35 receives at its input 48 a signal which indicates the proper operation of the film camera 23, shown again in FIG. 2 by broken lines. At the input 49 lies a signal which indicates whether or not a film cassette has been inserted. The signal at the input 50 shows whether there is enough film in the film cassette. When there is proper operation and the film camera 23 is properly supplied, the AND gate 35 supplies a signal through the OR gate 33 for the opening of the switch transistor 38, so that there is quiet illumination of the lamp 19 and thus of the picture 15 of the film camera 23.

When one of the signals disappears at the input 48 to 50, namely, when there is a disturbance in the camera, when there is no film cassette, or when it does not have sufficient film any more, the AND gate 34 supplies to the AND gate 31 a signal which, in case of a properly selected photographing system, connects the pulse generator 41 through the OR gate 33 to the switch transistor 38. In that case, namely, when there is a disturbance in the film camera 23, the lamp 19 blinks and thus, the picture 15 of the film camera 23 also blinks.

If, in a prepared photographing system, the diaphragm 21 is closed, there is no signal in the line 40, so that the pulse generator 41 causes, through the AND gate 29 and the switch transistor 36, the blinking of the lamp 17, so that the picture 13 of the diaphragm 21 will blink.

It is apparent that the quiet illumination of the pictures 12 to 15 upon the operating desk indicates a proper operation or preparedness for the making of a sequence of cinema pictures. When there is no proper selection of the photographing system, namely, connection to the central high-voltage generator 24, none of the lamps 16 to 19 will light, and thus, none of the pictures 12 to 15 will be illuminated. If there is a disturbance, if the diaphragm 21 is closed, if during the preparation of a photographing sequence no balance through the dose control device has been reached, if the camera 23 does not operate properly, if no film cassette has been inserted, or if there is insufficient film therein, in all these instances, the corresponding lamps 17 to 19 will blink. Thus, the readiness for operation of the X-ray diagnosing apparatus and operation without disturbances are indicated by permanent light behind the pictures 12 to 15, while disturbances are indicated by blinking light or by complete extinguishing of the corresponding lamps.

The user of the X-ray diagnosing apparatus can determine at the operating desk, by a single glance, whether the specific X-ray diagnosing apparatus is ready for operation or operates properly; for example, if a film cassette has been placed into the film camera, if the diaphragm has been opened, etc. Thus, the supervision of the X-ray diagnosing apparatus is very simple.

The present invention has been described in connection with a photographing system for making X-ray motion pictures. However, it can be used generally whenever a photographing system of any type is to be be supervised from an operating desk carrying selectable photographing data.

The high-voltage generator 24 is of known construction. The control of the brightness upon the output screen of the X-ray image intensifier 22 takes place in a known manner by comparing the outgoing signal of the photomultiplier 51 with a rated value signal which embodies the rated value of this brightness. The ray intensity is changed automatically in adaptation to both of these signals. To the high-voltage generator 24, in addition to members 20 to 23, which represent a photographing system, are corelated in a known manner further photographing systems which can be connected selectively. Switches corresponding to switches 25 and 26 are provided for these further photographing systems. Two of these switches are always selectively closed.

The photomultiplier 51 is well known in the art and is shown for example, under numeral 32 in FIG. 1 of U.S. Pat. No. 3,783,086. It is used for regulating the dose output of the X-ray source. When the regulating limits are reached, for example, when the X-ray current or X-ray voltage have reached specific limits, the signal at the inlet 44 of FIG. 2 of the present application disappears and this fact is indicated by blinking light.

Figure 3:
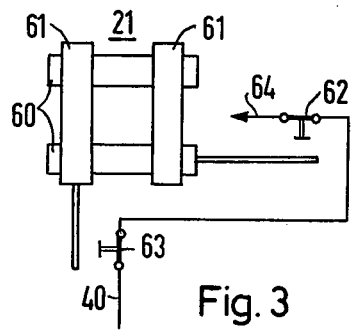
FIG. 3 is a diagram illustrating the transmission of the signal.

FIG. 3 shows in detail the diaphragm 21 and the producing of the signal upon the conduit 40. The diaphragm 21 consists of two diaphragm plate pairs 60 and 61, which can be shifted jointly toward and away from each other. During the shifting of diaphragm plate pair 60 a switch 62 can be actuated when the two diaphragm plates lie against each other, namely, when the diaphragm 21 is closed. In that case the contact 62 is opened. In a similar manner the contact 63 is opened when the two diaphragm plates 61 lie against each other, i.e. the diaphragm 21 is closed. The two contacts 62 and 63 are interconnected in series and are connected to a source of voltage by a conduit 64. Thus when the diaphragm 21 is opened the two contacts 62 and 63 assume the illustrated closed position and upon the conduit 40 will lie a signal which continuously keeps the lamp 17 switched on. When the diaphragm 21 is closed the signal upon the conduit 40 disappears and the lamp will blink in the described manner.

Figure 4:
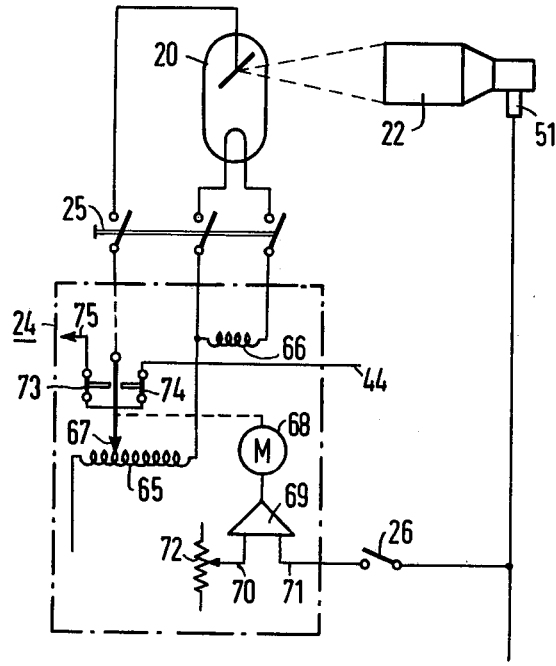
FIG. 4 is a circuit showing the connections of the generator.

FIG. 4 shows in greater detail the dose output regulating device in the X-ray generator 24. The X-ray generator 24 includes a regulating transformer 65 which supplies the X-ray tube 20 with high voltage when the switch 25 is closed. The X-ray tube 20 is shown with its wiring in FIG. 4. The generator 25 also includes a heating transformer which supplies the X-ray tube with heating voltage when the switch 25 is closed. Only the secondary winding 66 of the heating transformer is shown in FIG. 4. For the sake of simplicity of illustration the switch 25 is shown in FIG. 1 as a single switch, while FIG. 4 shows that it consists of three individual switches.

The regulation of the dose output takes place by shifting the contact 67 of regulating transformer 65 by means of a regulating motor 68. The regulating motor 68 is operated by the outgoing signal of a comparator 69 which as a rated value inlet 70 and an actual value inlet 71. The rated value inlet 70 is connected to rated value giving means 72 for the dose output and thus for the brightness upon the outlet screen of the X-ray image intensifier 22. The actual value inlet 71 is connected by the switch 26 to the photo multiplier 51. The comparator 69 compares the actual value of brightness upon the outlet screen of the image intensifier 22 with the set rated value and actuates the motor 68 in such manner that the contact 67 is moved into a position in which the desired brightness and thus described dose output are produced. When the contact 67 reaches one of its two end locations either a switch 73 or a switch 74 is actuated. The switches 73 and 74 are interconnected in series and are connected with the conduit 44. Furthermore, they are connected by a conduit 75 with a voltage source. If during dose output regulations a balance is achieved, namely if the adjustable contact 67 does not reach any one of its limits, then there is a signal upon the conduit 44 which indicates this. If the contact 67 reaches one of its limits, then the switch 73 or the switch 74 is opened and this signal disappears, so that the lamp 18 will be caused to blink.

Figure 5:
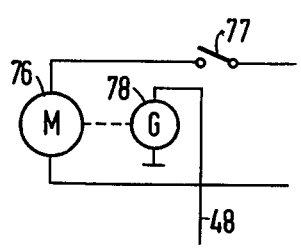
FIG. 5 is a diagram illustrating the formation of a signal.

FIG. 5 shows the formation of a signal upon the conduit 48. FIG. 5 shows an electric motor 76 which drives the film camera 23. When the switch 77 is closed this motor is switched on and will rotate. A generator 78 is coupled with the motor 76 and it produces an outgoing signal which indicates whether the motor 76 is rotated or is not rotated after the closing of the switch 77. If the motor stands still after the closing of the switch 77, then there is no signal in the conduit 48. The switch 77 is closed at the beginning of a photographing series. The generator 78 can be a tacho generator or an impulse producer.

Figure 6:
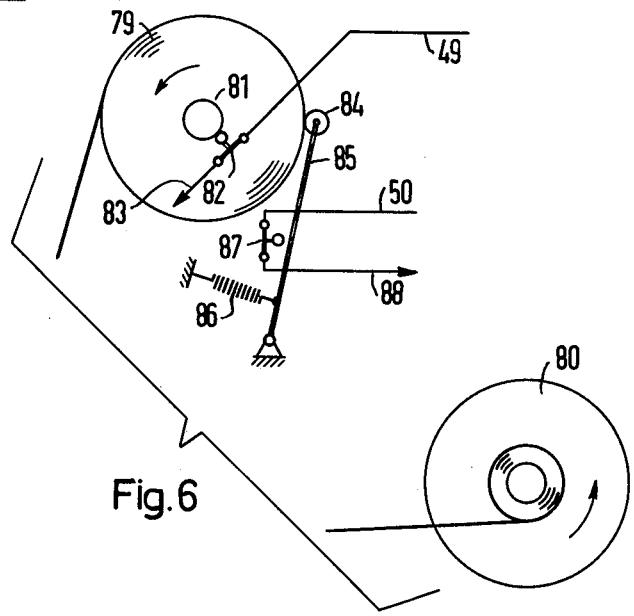
FIG. 6 is a diagram showing the operation of signals.

FIG. 6 shows the producing of signals upon conduits 49 and 50. It shows a full film roll 79 and an empty film roll 80. The motor 76 shown in FIG. 5 drives the film rolls 79 and 80 in the direction of the arrows, so that during the making of a motion picture scene the film moves from the full film roll 79 to the empty film roll 80. When the film roll 79 is shifted upon its shaft 81, a switch 82 is closed which is connected by a conduit 83 to a source of voltage and thus produces a signal upon the conduit 49. This signal disappears when the roll 79 is removed from the shaft 81 since then the switch 82 is opened.

A reel 84 engages the film upon the roll 79 and is rotatably fixed upon a lever 85. The lever 85 is engaged by a spring 86, thereby pressing the reel 84 against the film. When the supply of film upon the roll 79 reaches its lower limit the switch 87 is opened and then the signal upon the conduit 50 disappears, which had been supplied by a source of voltage through the conduit 88.

What is claimed is:

1. An X-ray diagnosing apparatus for several photographing systems selectively connected to a common generator, each of said systems comprising an X-ray tube, means connecting said X-ray tube to said generator, auxiliary devices for producing exposures, an operating desk for each photographing system having an indicating area, separate signaling lamps for said X-ray tube and said auxiliary devices within said indicating area and connecting means connecting said signaling lamps with the high-voltage generator for said X-ray tube and said auxiliary devices and operating said lamps to indicate operational readiness and trouble-free operation of said X-ray tube and said auxiliary devices in said indicating area, said auxiliary devices comprising film camera means, said indicating area having pictures representing the X-ray tube and the film camera means, one of said signaling lamps being adapted to illuminate the picture representing the X-ray tube and another of said signaling lamps being adapted to illuminate the picture representing said film camera means.

2. A system according to claim 1, wherein said film camera means is operable to receive a film supply and has switch means for actuation when a film supply is present, and said connecting means controlling illumination of said another of said signaling lamps and being responsive to said switch means so as to control the illumination of the picture representing said film camera means in accordance with whether or not a film supply is present on said film camera means.

3. A system according to claim 1, wherein said film camera means has a film quantity sensor for indicating the amount of unused film in its film supply, and said connecting means being responsive to said film quantity sensor to control the illumination of said another of said signaling lamps thereby to control the illumination of the picture representing said film camera means in accordance with the amount of unused film in the film supply of said film camera means.

* * * * *